(12) United States Patent
Minami et al.

(10) Patent No.: US 11,960,839 B2
(45) Date of Patent: Apr. 16, 2024

(54) CAUSE-EFFECT SENTENCE ANALYSIS DEVICE, CAUSE-EFFECT SENTENCE ANALYSIS SYSTEM, PROGRAM, AND CAUSE-EFFECT SENTENCE ANALYSIS METHOD

(71) Applicants: RESONAC CORPORATION, Tokyo (JP); School Juridical Person Seikei Gakuen, Tokyo (JP)

(72) Inventors: Takuya Minami, Tokyo (JP); Yoshishige Okuno, Tokyo (JP); Chinatsu Tanabe, Tokyo (JP); Yusuke Yamazaki, Tokyo (JP); Hiroyuki Sakai, Tokyo (JP); Hiroki Sakaji, Tokyo (JP)

(73) Assignees: Resonac Corporation, Tokyo (JP); School Juridical Person Seikei Gakuen, Musashino (JP)

( * ) Notice: Subject to any disclaimer, the term of this patent is extended or adjusted under 35 U.S.C. 154(b) by 456 days.

(21) Appl. No.: 16/758,462

(22) PCT Filed: Oct. 30, 2018

(86) PCT No.: PCT/JP2018/040285
§ 371 (c)(1),
(2) Date: Apr. 23, 2020

(87) PCT Pub. No.: WO2019/088084
PCT Pub. Date: May 9, 2019

(65) Prior Publication Data
US 2020/0257855 A1    Aug. 13, 2020

(30) Foreign Application Priority Data
Nov. 6, 2017   (JP) .................... 2017-214104

(51) Int. Cl.
*G06F 17/00* (2019.01)
*G06F 40/20* (2020.01)
(Continued)

(52) U.S. Cl.
CPC ............ *G06F 40/289* (2020.01); *G06F 40/20* (2020.01); *G16H 50/70* (2018.01)

(58) Field of Classification Search
CPC ........ G06F 40/289; G06F 40/20; G06F 40/30; G06F 16/00; G06F 16/30; G16H 50/70
See application file for complete search history.

(56) References Cited

U.S. PATENT DOCUMENTS 7,251,781 B2 *  7/2007  Batchilo ............... G06F 16/345
                                                    707/E17.094
9,524,345 B1 *  12/2016  VanderDrift ...... G06F 16/24578
(Continued)

FOREIGN PATENT DOCUMENTS

JP    2011-022668 A    2/2011
JP    2011-100368 A    5/2011
(Continued)

OTHER PUBLICATIONS

Fallucchi, Francesca, and Fabio Massimo Zanzotto. "Transitivity in semantic relation learning." In Proceedings of the 6th International Conference on Natural Language Processing and Knowledge Engineering (NLPKE-2010), pp. 1-8. IEEE, 2010. (Year: 2010).*
(Continued)

*Primary Examiner* — Andrew T McIntosh
(74) *Attorney, Agent, or Firm* — Sughrue Mion, PLLC

(57) ABSTRACT

A cause-effect sentence analysis device including: a cause-effect sentence extraction unit configured to extract a cause-effect sentence including a cause expression and an effect expression from a text; an acquisition unit configured to acquire information indicating a reference expression for
(Continued)

analyzing the degree of similarity; a similarity degree analysis unit, for a cause-effect sentence extracted by the cause-effect sentence extraction unit, configured to calculate a cause similarity degree, namely, the degree of similarity between the reference expression and the cause expression included in the cause-effect sentence, and an effect similarity degree, namely, the degree of similarity between the reference expression and the effect expression; and a desired cause-effect sentence extraction unit for extracting a cause-effect sentence in which one of the cause expression and the effect expression included in the cause-effect sentence is similar to the reference expression and the other is not similar to the reference expression.

15 Claims, 9 Drawing Sheets

(51) Int. Cl.
*G06F 40/289* (2020.01)
*G16H 50/70* (2018.01)

(56) References Cited

U.S. PATENT DOCUMENTS

| | | | | |
|---|---|---|---|---|
| 9,984,067 | B2* | 5/2018 | Visel | G06F 40/30 |
| 10,866,992 | B2* | 12/2020 | Pol | G06F 16/367 |
| 2003/0004915 | A1* | 1/2003 | Lin | G06F 16/36 |
| 2005/0071150 | A1* | 3/2005 | Nasypny | G06F 16/3344 |
| | | | | 707/E17.084 |
| 2005/0288915 | A1* | 12/2005 | Hines | H04L 41/0631 |
| | | | | 703/17 |
| 2006/0041424 | A1* | 2/2006 | Todhunter | G06F 40/30 |
| | | | | 707/E17.094 |
| 2007/0282814 | A1* | 12/2007 | Gupta | G06F 40/20 |
| 2008/0097951 | A1* | 4/2008 | Gupta | G06N 5/025 |
| | | | | 706/59 |
| 2012/0029908 | A1* | 2/2012 | Takamatsu | G06F 40/30 |
| | | | | 704/9 |
| 2012/0130936 | A1* | 5/2012 | Brown | G06Q 10/0633 |
| | | | | 706/52 |
| 2014/0039875 | A1* | 2/2014 | Hao | G06F 40/30 |
| | | | | 704/9 |
| 2015/0309992 | A1* | 10/2015 | Visel | G06F 40/30 |
| | | | | 704/9 |
| 2016/0012034 | A1* | 1/2016 | Andrade Silva | G06F 40/35 |
| | | | | 704/9 |
| 2016/0124937 | A1* | 5/2016 | Elhaddad | G06F 40/205 |
| | | | | 704/9 |
| 2016/0148111 | A1* | 5/2016 | Miyata | G06N 5/047 |
| | | | | 706/48 |
| 2016/0155058 | A1* | 6/2016 | Oh | G06N 20/00 |
| | | | | 706/11 |
| 2016/0259847 | A1* | 9/2016 | Fliri | G06F 16/358 |
| 2016/0357854 | A1* | 12/2016 | Hashimoto | G06F 16/3344 |
| 2017/0212928 | A1* | 7/2017 | Abebe | G06F 16/24549 |
| 2017/0220937 | A1* | 8/2017 | Wada | G06N 5/04 |
| 2017/0262754 | A1* | 9/2017 | Mizuno | G06F 40/30 |
| 2017/0308790 | A1* | 10/2017 | Nogueira dos Santos | |
| | | | | G06N 3/045 |
| 2017/0337180 | A1* | 11/2017 | Wang | G06F 40/247 |
| 2018/0082195 | A1* | 3/2018 | Kitagishi | G06N 5/04 |
| 2018/0285184 | A1* | 10/2018 | Hotta | G06F 11/3495 |
| 2018/0300427 | A1* | 10/2018 | Harbison | G06F 16/90335 |
| 2019/0073420 | A1* | 3/2019 | Agapiev | G06F 16/9024 |

FOREIGN PATENT DOCUMENTS

| | | |
|---|---|---|
| JP | 2015-011426 A | 1/2015 |
| JP | 2015-121897 A | 7/2015 |

OTHER PUBLICATIONS

Zhang, Yating, Adam Jatowt, and Katsumi Tanaka. "Causal relationship detection in archival collections of product reviews for understanding technology evolution." ACM Transactions on Information Systems (TOIS) 35, No. 1 (2016): 1-41. (Year: 2016).*
Zhao, Sendong, Quan Wang, Sean Massung, Bing Qin, Ting Liu, Bin Wang, and ChengXiang Zhai. "Constructing and embedding abstract event causality networks from text snippets." In Proceedings of the Tenth ACM International Conference on Web Search and Data Mining, pp. 335-344. 2017. (Year: 2017).*
Nohara, Shoji, and Ryosuke Saga. "Preprocessing method topic-based path model by using Word2vec." In Proceedings of The International MultiConference of Engineers and Computer Scientists 2017, pp. 15-17. 2017. (Year: 2017).*
Yordanova, Kristina. "Discovering causal relations in textual instructions." Proceedings of the international conference recent advances in natural language processing. 2015 (Year: 2015).*
Asghar, Nabiha. "Automatic extraction of causal relations from natural language texts: a comprehensive survey." arXiv preprint arXiv:1605.07895 (2016) (Year: 2016).*
Zhao, Sendong, et al. "Event causality extraction based on connectives analysis." Neurocomputing 173 (2016): 1943-1950 (Year: 2016).*
Daisuke Ishikawa et al., "Generation and Verification of a hypothesis by Analogical Reasoning using Casual Relationships in Patent Documents—Life Science Fields as an Example-", Joho Chishiki Gakkaishi, 2007, pp. 164-181, vol. 17, No. 3.
Daisuke Ishikawa et al., "Extraction and Integration of Casual Relationships in Patent Documents", Joho Chishiki Gakkaishi, Japan Society of Information and Knowledge, 2004, pp. 105-118, vol. 14, No. 4.
International Search Report for PCT/JP2018/040285, dated Jan. 22, 2019.

* cited by examiner

FIG. 3

| | CAUSE EXPRESSION | RESULT EXPRESSION |
|---|---|---|
| EXAMPLE 1 | AS THE AMOUNT OF USED CARBON ... IS EQUAL TO OR SMALLER THAN AN UPPER LIMIT ..., | ... AND THUS, IT IS POSSIBLE TO RETAIN INSULATION IN A CASE WHERE IT IS USED AS A THERMALLY-CONDUCTIVE FILLER. |
| EXAMPLE 2 | ACCORDING TO THE INVENTOR, DUE TO FORMATION ..., | ... IT IS POSSIBLE TO OBTAIN A THERMALLY-CONDUCTIVE MATERIAL. |
| EXAMPLE 3 | AS DESCRIBED ABOVE, ... IT IS POSSIBLE TO DEPOSIT A FILM. | ... TO THEREBY MAKE IT POSSIBLE TO REDUCE A THERMAL CONDUCTIVITY OF A HEAT INSULATING LAYER. |
| EXAMPLE 4 | SINCE THREE-DIMENSIONAL ACICULAR METAL OXIDE (D) ... CAN FORM A THERMALLY-CONDUCTIVE NETWORK. | ... IT IS POSSIBLE TO ENHANCE THERMAL CONDUCTION |
| EXAMPLE 5 | ... BY CHANGING THE RATE OR AMOUNT OF SURFACE PROCESSING. | ... IT IS POSSIBLE TO PROVIDE A POLYMER STRUCTURE |
| EXAMPLE 6 | ... SINCE PORES ARE REDUCED. | ... IT IS POSSIBLE TO ENHANCE THERMAL CONDUCTIVITY. |
| EXAMPLE 7 | ... BY PERFORMING SOLID-PHASE SINTERING. | ... A HEAT DISSIPATING BOARD IS OBTAINED. |

FIG. 4

| PRIORITY | APPLICATION NUMBER OF EXTRACTED DOCUMENT | CAUSE EXPRESSION | RESULT EXPRESSION |
|---|---|---|---|
| 5 | PATENT APPLICATION NUMBER OO-XXXX | SIMILARITY DEGREE: 10 | SIMILARITY DEGREE: 1 |
| 4 | PATENT APPLICATION NUMBER OO-XXXX | SIMILARITY DEGREE: 9 | SIMILARITY DEGREE: 1 |
| 3 | PATENT APPLICATION NUMBER OO-XXXX | SIMILARITY DEGREE: 8 | SIMILARITY DEGREE: 1 |
| 2 | PATENT APPLICATION NUMBER OO-XXXX | SIMILARITY DEGREE: 7 | SIMILARITY DEGREE: 1 |
| 1 | PATENT APPLICATION NUMBER OO-XXXX | SIMILARITY DEGREE: 6 | SIMILARITY DEGREE: 2 |

FIG. 6   EXAMPLE OF CAUSE-EFFECT SENTENCE THAT MEETS PREDETERMINED CONDITION

| CAUSE-EFFECT SENTENCE | CAUSE EXPRESSION | RESULT EXPRESSION | SCORE |
|---|---|---|---|
| According to the invention, by hydrothermally synthesizing aqua gel that contains a transition metal raw material and polyamine with a Zeolite raw material to perform dispersion of transition metal into Zeolite pores together with synthesis of Zeolite in a Zeolite hydrothermal synthesis process, it is possible to easily and efficiently manufacture silicoaluminophosphate zeolite containing transition metal having high-temperature hydrothermal durability and excellent catalytic activity. (Sentence TX1) | According to the invention, by hydrothermally synthesizing aqua gel that contains a transition metal raw material and polyamine with a Zeolite raw material. (Sentence TX1-1) | to perform dispersion of transition metal into Zeolite pores together with synthesis of Zeolite in a Zeolite hydrothermal synthesis process, it is possible to easily and efficiently manufacture silicoaluminophosphate zeolite containing transition metal having high-temperature hydrothermal durability and excellent catalytic activity. (Sentence TX1-2) | 2.585138 (Score SC1) |
| Further, since the size of a nanoparticle is appropriately reduced, it is possible to enhance physical stability of the nanoparticle and to reliably maintain flatness of the surface of an optically extracted object, and thus, it is possible to enhance long-term reliability of a semiconductor light emitting element. (Sentence TX2) | Further, since the size of a nanoparticle is appropriately reduced, it is possible to enhance physical stability of the nanoparticle and to reliably maintain flatness of the surface of an optically extracted object, (Sentence TX2-1) | and thus, it is possible to enhance long-term reliability of a semiconductor light emitting element. (Sentence TX2-2) | 2.468314 (Score SC2) |

FIG. 7

EXAMPLE OF CAUSE-EFFECT SENTENCE THAT MEETS PREDETERMINED CONDITION

| CAUSE-EFFECT SENTENCE | CAUSE EXPRESSION | RESULT EXPRESSION | SCORE |
|---|---|---|---|
| A broken line surrounded to show a light emitting part 5 is for showing the light emitting part 5 for convenience, and is not for showing an element that configures a lighting system 1. (Sentence TX3) | A broken line surrounded to show a light emitting part 5 is for showing the light emitting part 5 for convenience. (Sentence TX3-1) | and is not for showing an element that configures a lighting system 1. (Sentence TX3-2) | -2.17691 (Score SC3) |
| A positioning hub 783 is engaged with a positioning pin 574 formed on a shaft side rear wall 546 of a main body frame 3, and similarly, a stop hole 782 corresponds to a passage unit attachment hub 562 formed on the shaft side rear wall 546. (Sentence TX4) | A positioning hub 783 is engaged with a positioning pin 574 formed on a shaft side rear wall 546 of a main body frame 3. (Sentence TX4-1) | and similarly, a stop hole 782 corresponds to a passage unit attachment hub 562 formed on the shaft side rear wall 546. (Sentence TX4-2) | -2.18209 (Score SC4) |

FIG. 8

CAUSE EXPRESSION  RESULT EXPRESSION

It is possible to prevent attachment of adhesive substances,
           to thereby make it possible to finish maintenance to the minimum.

It is possible to prevent attachment of adhesive substances, DEGREE OF IMPORTANCE OF CAUSE SENTENCE 5.0
       1.0  1.0   3.0 to thereby make it possible to finish maintenance to the minimum. DEGREE OF IMPORTANCE OF RESULT SENTENCE 8.5
         0.5  5.0    3.0

FIG. 9

QUERY

| CAUSE SENTENCE | RESULT SENTENCE | CAUSE SENTENCE KEYWORD | RESULT SENTENCE KEYWORD |
|---|---|---|---|
| Since the carbon nanotube manufactured in this way does not contain solid carbon or a block object as impurities and has high electrical conductivity and thermal conductivity, it is possible to cause the carbon nanotube to be contained in a matrix of resin, metal, ceramics, or the like to obtain a composite material, | to thereby make it possible to enhance conductivity or thermal conductivity of resin, metal, ceramics, or the like. | CARBON NANOTUBE | (NONE) |

EXTRACTION RESULT OF CAUSAL SENTENCE OF SIMILAR CAUSE AND DISSIMILAR RESULT

| CAUSE SENTENCE | RESULT SENTENCE |
|---|---|
| As described above, as a resin composition for an electromagnetic shield that contains the composite carbon material of the invention can be used as a composite material on the basis of the carbon nanotube of which the surface is improved under the condition that an oxidizing agent is not used, a carbon compound, a metal, a metal compound, or a composite thereof. | excellent dispersibility and shock mitigating characteristics, and high conductivity are obtained, and particularly, an effect of an electromagnetic shield is achieved. |

CAUSE-EFFECT SENTENCE ANALYSIS DEVICE, CAUSE-EFFECT SENTENCE ANALYSIS SYSTEM, PROGRAM, AND CAUSE-EFFECT SENTENCE ANALYSIS METHOD

CROSS REFERENCE TO RELATED APPLICATIONS

This application is a National Stage of International Application No. PCT/JP2018/040285 filed Oct. 30, 2018, claiming priority based on Japanese Patent Application No. 2017-214104 filed Nov. 6, 2017.

TECHNICAL FIELD

The present invention relates to a cause-effect sentence analysis device, a cause-effect sentence analysis system, a program, and a cause-effect sentence analysis method.

BACKGROUND ART

A technique for extracting a cause-effect sentence including a pair of cause information (means) and effect information (effect) from a patent document using a computer is known (for example, Patent Document 1).

Further, a technique for extracting a cause-effect relationship between means and an effect from a patent literature and inferring that a cause-effect relationship having similar means has a similar effect using a computer is known (for example, Non-Patent Document 1).

CITATION LIST

Patent Literature

[Patent Document 1]
Japanese Unexamined Patent Application First Publication No. 2011-22668

Non Patent Literature

[Non Patent Document 1]
Daisuke Ishikawa, et al., "Generation and Verification of Hypothesis by Analogical Reasoning using Causal Relationships in Patent Documents": Journal of Japan Society of Information and Knowledge, 2007, Vol. 17, No. 3, p. 164-181

SUMMARY OF INVENTION

Technical Problem

Here, there is a case where, hi regard to a document group including a cause-effect sentence including a pair of cause information and effect information, a document having a similar cause expression (means) and a different effect expression (effect) compared with a certain document (document A) is extracted, so that the extracted document may be used for studying a new use of a technique disclosed in the document A. Further, there is a case where a document having a similar effect expression (effect) and a different cause expression (means) compared to a certain document (document B) is extracted, so that the extracted document may be used for studying different technical configurations in which the same effect as that of the document B may be obtained.

The invention has been made in view of the above problems, and an object of the invention is to provide a cause-effect sentence analysis device, a cause-effect sentence analysis system, a program, and a cause-effect sentence analysis method for extracting a document that meets a desired condition.

Solution to Problem (1) A cause-effect sentence analysts device according to an aspect of the invention includes: a cause-effect sentence extraction unit that is configured to extract a cause-effect sentence including a cause expression and an effect expression from a text; an acquisition unit that is configured to acquire information indicating a reference expression serving as a reference for analyzing a degree of similarity; a similarity degree analysis unit that is configured to calculate, for the cause-effect sentence extracted by the cause-effect sentence extraction unit, a cause similarity degree that is the degree of similarity between the cause expression included in the cause-effect sentence and the reference expression and an effect similarity degree that is the degree of similarity between the effect expression included in the cause-effect sentence and the reference expression; and a desired cause-effect sentence extraction unit that is configured to extract a cause-effect sentence in which one of the cause expression and the effect expression included in the cause-effect sentence is similar to the reference expression and the other is not similar to the reference expression. Thus, it is possible to extract a document that meets a desired condition.

(2) In the cause-effect sentence analysis device according to the aspect of the invention, the reference expression may include a cause expression and an effect expression.

(3) In the cause-effect sentence analysts device according to the aspect of the invention, the desired cause-effect sentence extraction unit may extract a cause-effect sentence in which one of the cause similarity degree and the effect similarity degree is equal to or greater than a first threshold and the other thereof is equal to or smaller than a second threshold which is smaller than the first threshold.

(4) The cause-effect sentence analysis device according to the aspect of the invention further may include a cause-effect relationship extraction unit that is configured to extract a cause-effect sentence that meets a predetermined condition from the cause-effect sentences extracted by the cause-effect sentence extraction unit, in winch the similarity degree analysis unit may calculate the cause similarity degree and the effect similarity degree for the cause-effect sentence extracted by the cause-effect relationship extraction unit.

(5) The cause-effect sentence analysis device according to the aspect of the invention may further include: an importance degree calculation unit that is configured to calculate a degree of importance of the cause-effect sentence extracted by the cause-effect sentence extraction unit; and an important cause-effect sentence extraction unit that is configured to extract a cause-effect sentence having a high importance degree from the cause-effect sentences extracted by the cause-effect relationship extraction unit on the basis of the degree of importance calculated by the importance degree calculation unit, in which the similarity degree analysis unit may calculate the cause similarity degree and the effect similarity degree for the cause-effect sentence extracted by the important cause-effect sentence extraction unit as the cause-effect sentence having the high importance degree.

(6) The cause-effect sentence analysis device according to the aspect of the invention may further include a query extraction unit that is configured to extract a query on the basis of the cause-effect sentence extracted by the cause-effect sentence extraction unit, in which the acquisition unit may acquire the query extracted by the query extraction unit as the reference expression.

(7) In the cause-effect sentence analysis device according to the aspect of the invention, the acquisition unit may acquire information input by a user as information indicating the reference expression.

(8) In the cause-effect sentence analysis device according to the aspect of the invention, the acquisition unit may acquire information indicating a keyword input to the cause-effect sentence analysis device by the user as information indicating the reference expression.

(9) The cause-effect sentence analysis device according to the aspect of the invention may further include: a priority assigning unit that is configured to assign a priority on the basis of the cause similarity degree and the effect similarity degree to the cause-effect sentence of which the came similarity degree and the effect similarity degree are calculated by the similarity degree analysis unit.

(10) In the cause-effect sentence analysis device according to the aspect of the invention, the priority assigning unit may assign the priority to a cause-effect sentence having an effect expression that is similar to the reference expression and a cause expression that is not similar to the reference expression among the cause-effect sentences of which the cause similarity degree and the effect similarity degree are calculated by the similarity degree analysis unit, in an ascending order of the cause similarity degree.

(11) In the cause-effect sentence analysis device according to the aspect of the invention, the priority assigning unit may assign the priority to a cause-effect sentence having a cause expression that is similar to the reference expression and an effect expression that is not similar to the reference expression among the cause-effect sentences of which the cause similarity degree and the effect similarity degree are calculated by the similarity degree analysis unit, in an ascending order of the effect similarity degree.

(12) in the cause-effect sentence analysis device according to the aspect of the invention, the text may be a sentence included in a patent document.

(13) A cause-effect sentence analysis system according to an aspect of the invention may include the above-described cause-effect sentence analysts device; an input unit for inputting information indicating the reference expression; and a display unit that is configured to display the cause-effect sentence output by the cause-effect sentence analysis device. Thus, it is possible to extract a document that meets a desired condition.

(14) A program according to an aspect of the invention that causes a computer to execute; a cause-effect sentence extraction step of extracting a cause-effect sentence including a cause expression and an effect expression from a text; an acquisition step of acquiring information indicating a reference expression serving as a reference for analyzing a degree of similarity; a similarity degree analysis step of calculating, for the extracted cause-effect sentence, a cause similarity degree that is the degree of similarity between the cause expression included in the cause-effect sentence and the reference expression and an effect similarity degree that is the degree of similarity between the effect expression included in the cause-effect sentence and the reference expression; and an output step of extracting a cause-effect sentence in which one of the cause expression and the effect expression included in the cause-effect sentence is similar to the reference expression and the other is not similar to the reference expression.

(15) A cause-effect sentence analysis method performed in a computer, including: extracting a cause-effect sentence including a cause expression and an effect expression from a text; acquiring information indicating a reference expression serving as a reference for analyzing the degree of similarity; calculating, for the extracted cause-effect sentence, a cause similarity degree that is the degree of similarity between the cause expression included in the cause-effect sentence and the reference expression and an effect similarity degree that is the degree of similarity between the effect expression included in the cause-effect sentence and the reference expression; and extracting and outputting a cause-effect sentence in which one of the cause expression and the effect expression included in the cause-effect sentence is similar to the reference expression and the other is not similar to the reference expression.

Advantageous Effects of Invention

According to the invention, it is possible to provide a cause-effect sentence analysis device, a cause-effect sentence analysis system, a program, and a cause effect sentence analysis method for extracting a document that meets a desired condition.

BRIEF DESCRIPTION OF DRAWINGS

FIG. 3 is a diagram showing an example of a cause-effect sentence.

FIG. 4 is a diagram showing an example of an image displayed on a display unit.

FIG. 6 is a diagram showing an example of a cause-effect sentence that meets a predetermined condition according to the embodiment.

FIG. 7 is a diagram showing an example of a cause effect sentence that does not meet the predetermined condition according to the embodiment.

FIG. 8 is a diagram showing an example of calculation of the degree of importance of a cause-effect sentence according to the embodiment.

FIG. 9 is a diagram showing an output example of a cause-effect sentence according to the embodiment.

DESCRIPTION OF EMBODIMENTS

Embodiment

Hereinafter, embodiments of the invention will be described with reference to the drawings.

[Overview of Cause-Effect Sentence Analysis Device]

Figure 1:
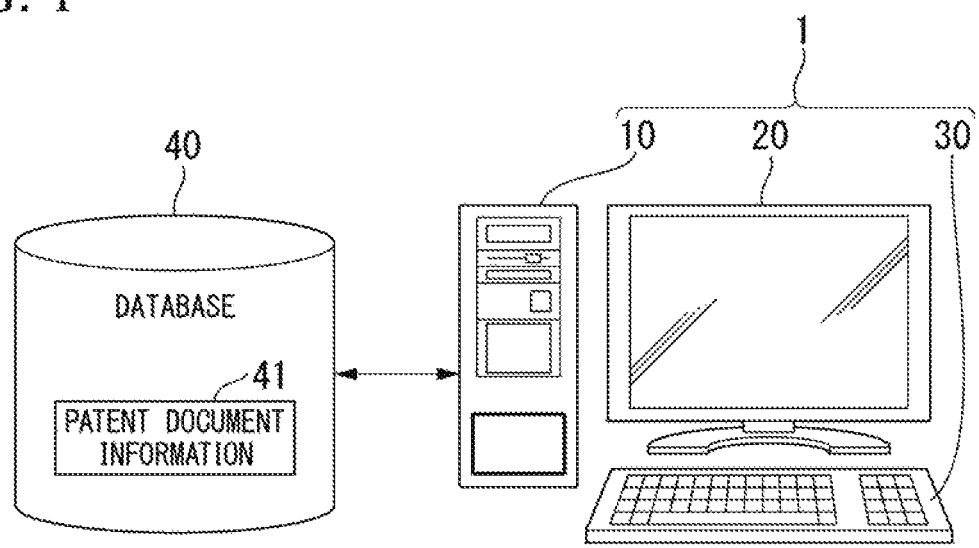
FIG. 1 is a diagram showing an overview of a cause-effect sentence analysis system according to an embodiment.

FIG. 1 is a diagram showing an overview of a cause-effect sentence analysis system 1 according to an embodiment.

As shown in FIG. 1, the cause-effect sentence analysis system 1 includes a cause-effect sentence analysis device 10, a display unit 20, and an operation unit 30. The cause-effect sentence analysis device 10 is, for example, provided in an information processing device such as a workstation, a desktop PC (Personal Computer), a notebook PC, a tablet PC, a multifunctional mobile phone terminal (smartphone), an electronic book leader with a communication function, a PDA (Personal Digital Assistant), or the like. The display unit 20 and the operation unit 30 are connected to the cause-effect sentence analysis device 10 (information processing device). The display unit 20 displays various images under the control of the cause-effect sentence analysis device 10. The operation unit 30 supplies information indicating an operation input through the operation unit 30 by a user of the cause-effect sentence analysis device 10 to the cause-effect sentence analysis device 10. In the following description, the user of the cause-effect sentence analysis device 10 will be simply referred to as a user. Here, the operation unit 30 is an example of an input unit.

A database 40 is connected to the cause-effect sentence analysis device 10 so that information can be transmitted and received therebetween. The database 40 stores, for example, information (hereinafter, patent document information 41) indicating a document relating to a patent (hereinafter, a patent document). The patent document includes, for example, a patent publication gazette, an unexamined patent application publication gazette, and the like. In an example of the present embodiment, the patent document information 41 is information in which a plurality of patent documents and identification information (for example, a patent number, an unexamined patent application publication number, a patent application number, and the like) of the patent documents are associated with each other. The database 40 may be realized by a random access memory (RAM), a read only memory (ROM), a hard disk drive (HDD), a flash memory, or a hybrid storage device in which a plurality of these memories are combined.

[Study of New Uses of Invention and Study of Different Configurations of Invention]

A patent document shows texts representing detailed content such as a problem to be solved by the invention, means for solving the problem, an embodiment for carrying out the invention, an effect of the invention, and the like. Specifically, the texts of the patent document include cause-effect sentences that include means and embodiments as cause expressions and include effects as effect expressions, cause-effect sentences that include effects as cause expressions and include derivative effects such as uses as effect expressions, cause-effect sentences that include means and embodiments as cause expressions and include derivative effects such as uses as effect expressions, or the like. Here, there is a case where a user of a patent literature wants to refer to, on the basis of a patent document (for example, a patent document A) of a certain patent, a patent document (for example, a patent document B) that includes a cause-effect sentence having a similar cause expression and a non-similar (dissimilar) effect expression compared with a cause-effect sentence included in the patent document A. With respect to the patent document A, the patent document B is a patent document in which an invention that includes the same means or embodiment (that is, configuration) and achieves a different effect is disclosed. That is, there is a case where the user of the patent literature wants to refer to the patent document B as a reference resource for examining a new use of an invention disclosed in the patent document A.

Further, there is a case where the user of the patent literature wants to refer to, on the basis of a patent document (for example, a patent document A) of a certain patent, a patent document (for example, a patent document C) that includes a cause-effect sentence having a similar effect expression and a non-similar (dissimilar) cause expression compared with a cause-effect sentence included in the patent document A. With respect to the patent document A, the patent document C is a patent document in which an invention that achieves the same effect and includes a different configuration is disclosed. That is, there is a case where the user of the patent literature wants to refer to the patent document C as a reference for examining different configurations of an invention disclosed in the patent document A.

The cause-effect sentence analysis device 10 according to the present embodiment extracts, among cause-effect sentences included in a text of a certain patent document, a cause-effect sentence having a similar cause expression compared with a reference expression that serves as a comparison reference and a non-similar effect expression compared with a reference expression that serves as a comparison reference. Further, the cause-effect sentence analysis device 10 of the present embodiment extracts a cause-effect sentence having a similar effect expression and a non-similar cause expression among the cause-effect sentences included in the text of the certain patent document.

[Configuration of Cause-Effect Sentence Analysis Device]

Hereinafter, a configuration of the cause-effect sentence analysis system 1 will be described in detail with reference to FIG. 1.

Figure 2:
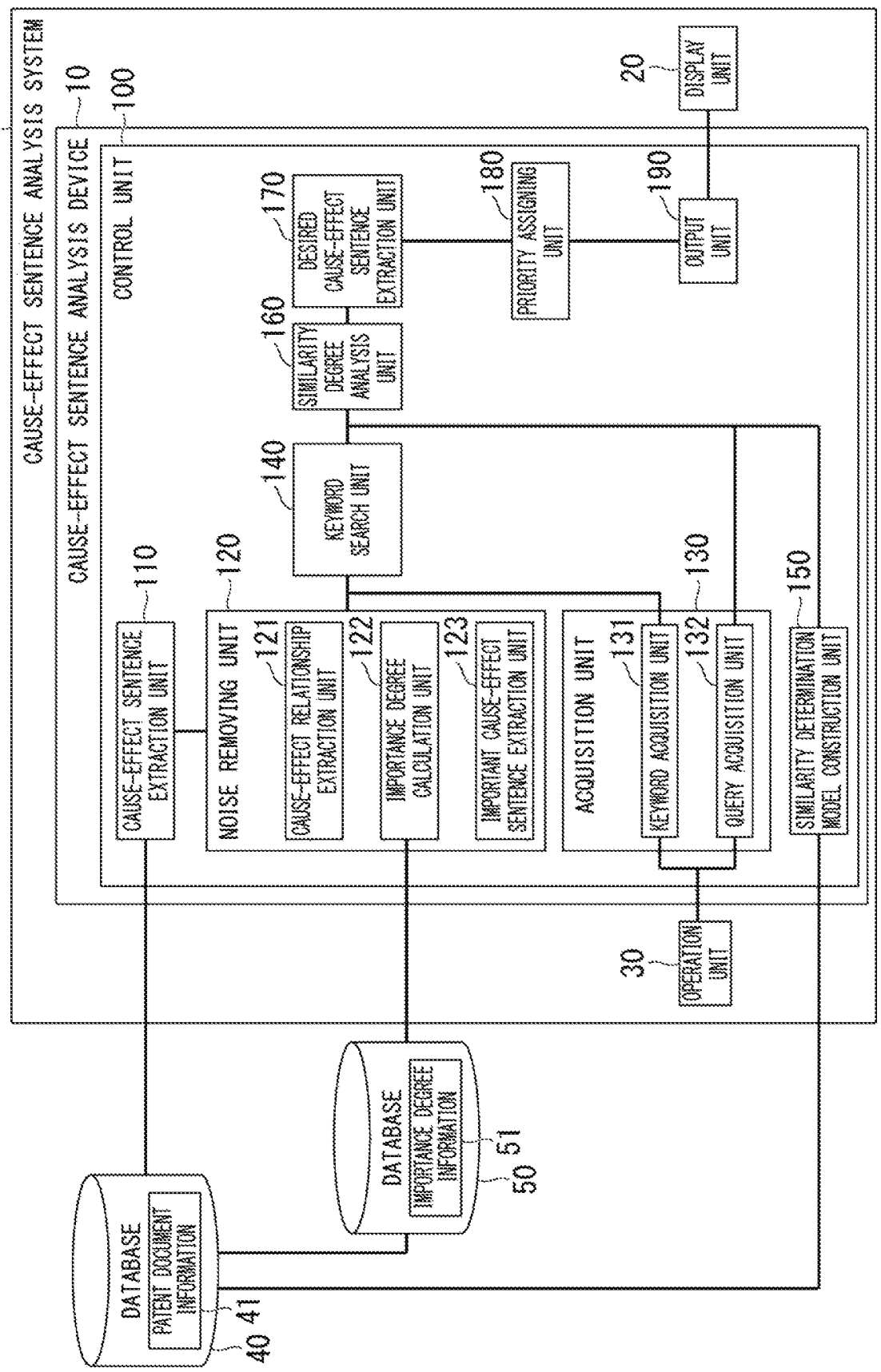
FIG. 2 is a diagram showing an example of a configuration of the cause-effect sentence analysis system according to the embodiment.

FIG. 2 is a diagram showing an example of a configuration of the cause-effect sentence analysis system 1 according to the embodiment.

As shown in FIG. 2, the cause-effect sentence analysis system 1 includes the cause-effect sentence analysis device 10, the display unit 20, and the operation unit 30. To the cause-effect sentence analysis device 10, the display unit 20, the operation unit 30, the database 40, and a database 50 are connected.

The database 50 stores information indicating the degree of importance of a word included in a patent document (hereinafter, importance degree information 51). Here, even in a case where a certain patent document and another patent document include the same word in the patent documents, the degrees of importance of the word in the patent documents may be different from each other. Accordingly, the importance degree information 51 indicates, for each patent document included in the patent document information 41, the degree of importance of each word included in the patent document. The degree of importance of a word included in a patent document is calculated for each patent document by a method using TF-IDF (Term Frequency-Inverse Document Frequency), for example. In one example of the present embodiment, the importance degree information 51 is information in which the degree of importance of each word included in the patent document is associated with identification information of the patent document.

The cause-effect sentence analysis device 10 includes a control unit 100. The control unit 100 executes a program stored in a storage unit (not shown) by a processor such as a CPU (Central Processing Unit), for example, and realizes a cause-effect sentence extraction unit 110, a noise removing unit 120, an acquisition unit 130, a keyword search unit 140, a similarity determination model construction unit 150, a similarity degree analysis unit 160, a desired cause-effect sentence extraction unit 170, a priority assigning unit 180, and an output unit 190 as functional units. These functional units may be realized by hardware such as LSI (Large Scale Integration), ASIC (Application Specific Integrated Circuit), FPGA (Field-Programmable Gate Array), or may be realized by cooperation of software and hardware.

The cause-effect sentence extraction unit 110 extracts a cause-effect sentence included in a patent document indicated by the patent document information 41. Hereinafter, examples of cause-effect sentences will be described with reference to the drawings.

FIG. 3 is a diagram showing examples of cause-effect sentences. The cause-effect sentence extraction unit 110 extracts a cause-effect sentence (Example 1 shown in the figure) in which a cause expression ("as") and an effect expression ("it is possible to") are included in the order of the cause expression and the effect expression, for example. In addition, the cause-effect sentence extraction unit 110 extracts a cause-effect sentence (Example 2 shown in the figure) in which a cause expression ("due to") and an effect expression ("it is possible to") are included in the order of the cause expression and the effect expression, for example. Further, the cause-effect sentence extraction unit 110 extracts a cause-effect sentence (Example 3 shown in the figure) in which a cause expression ("it is possible to") and an effect expression ("to thereby make it possible to") are included in the order of the cause expression and the effect expression, for example. Further, the cause-effect sentence extraction unit 110 also extracts a cause-effect sentence (Example 4 shown in the figure) in which a cause expression ("since it is possible to") and an effect expression ("it is possible to") are included in the order of the cause expression and the effect expression, for example.

Further, the cause-effect sentence extraction unit 110 extracts a cause-effect sentence (Example 5 shown in the figure) in which a cause expression ("by doing") and an effect expression ("it is possible to") are included in the order of the cause expression and the effect expression, for example, furthermore, the cause-effect sentence extraction unit 110 may also extract a cause-effect sentence (Example 6 shown in the figure) in which a cause expression ("since") and an effect expression ("it is possible to") are included in the order of the cause expression and the effect expression, for example. In addition, the cause-effect sentence extraction unit 110 extracts a cause-effect sentence (Example 7 shown in the figure) in which a cause expression ("by doing") and an effect expression ("is") are included in the order of the cause expression and the effect expression, for example.

Returning to FIG. 2, the noise removing unit 120 excludes cause-effect sentences other than a cause-effect sentence to be analyzed by the similarity degree analysis unit 160 from the cause-effect sentences extracted by the cause-effect sentence extraction unit 110. The noise removing unit 120 includes, for example, a cause-effect relationship extraction unit 121, an importance degree calculation unit 122, and an important cause-effect sentence extraction unit 123.

The cause-effect relationship extraction unit 121 extracts a cause-effect sentence that meets a predetermined condition from the cause-effect sentences extracted by the cause-effect sentence extraction unit 110. The cause-effect sentence that meets the predetermined condition is, for example, a cause-effect sentence in which a cause expression indicates a problem of an invention and an effect expression indicates an effect of the invention. The cause-effect relationship extraction unit 121 extracts the cause-effect sentence that meets the predetermined condition from the cause-effect sentences extracted by the cause-effect sentence extraction unit 110 by machine learning such as a support vector machine using teacher data, for example.

The importance degree calculation unit 122 calculates the degree of importance of a cause-effect sentence extracted by the cause-effect relationship extraction unit 121. Specifically, the importance degree calculation unit 122 refers to a patent document from which the cause-effect sentence is extracted from the importance degree information 51 stored in the database 50. The importance degree calculation unit 122 calculates the sum of the degrees of importance of words included in the cause-effect sentence on the basis of the importance degree information 51. The importance degree calculation unit 122 supplies the calculated sum of the degrees of importance to the important cause-effect sentence extraction unit 123 as the degree of importance of the cause-effect sentence.

The important cause-effect sentence extraction unit 123 extracts a cause-effect sentence to be analyzed by the similarity degree analysis unit 160 from the cause-effect sentences extracted by the cause-effect relationship extraction unit 121 on the basis of the degree of importance calculated by the importance degree calculation unit 122. Specifically, the important cause-effect sentence extraction unit 123 determines a cause-effect sentence in which at least one of a cause expression or an effect expression has the degree of importance equal to or greater than a predetermined threshold from the cause-effect sentences extracted by the cause-effect relationship extraction unit 121, as an analysis target of the similarity degree analysis unit 160. The important cause-effect sentence extraction unit 123 according to the present embodiment extracts a cause-effect sentence of which the degree of importance is equal to or greater than a predetermined threshold, and supplies the extracted cause-effect sentence to the keyword search unit 140. Further, the important cause-effect sentence extraction unit 123 does not extract a cause-effect sentence of which the degree of importance is smaller than the predetermined threshold from the cause-effect sentences extracted by the cause-effect relationship extraction unit 121 (that is, does not supply the cause-effect sentence to the keyword search unit 140).

The acquisition unit 130 includes a keyword acquisition unit 131 and a query acquisition unit 132. The keyword acquisition unit 131 acquires information indicating a keyword on the basis of an operation on the operation unit 30. The keyword is a known word or phrase included in a patent document indicated by the patent document information 41, which is a word or phrase to be used in a case where the cause-effect sentence analysis device 10 determines a patent document desired by a user. The keyword acquisition unit 131 according to the present embodiment acquires two keywords of a keyword (for example, "by", "due to", or "becomes possible, and thus") included in a cause expression and a keyword (for example, "can", "it is possible to", or the like) included in an effect expression.

The query acquisition unit 132 acquires information indicating a query on the basis of an operation on the operation unit 30. The query is a sentence to be used in a case where the cause-effect sentence analysis device 10 determines a patent document desired by a user, which is a sentence including at least a cause expression and an effect expression (that is, a cause-effect sentence). In the following description, a set of a keyword included in a cause expression and a keyword included in an effect expression, and a query including a cause expression and an effect expression are collectively referred to as a reference expression, and information indicating the reference expression is referred to as reference expression information.

The keyword search unit 140 acquires reference information acquired by the acquisition unit 130. The keyword search unit 140 acquires a cause-effect sentence extracted by the important cause-effect sentence extraction unit 123. The keyword search unit 140 extracts a cause-effect sentence to be analyzed by the similarity degree analysis unit 160 from the acquired cause-effect sentences on the basis of the reference information. Specifically, in a case where a cause expression or an effect expression of the acquired cause-effect sentence includes the reference expression, among the acquired cause-effect sentences, the keyword search unit 140 supplies the cause-effect sentence to the similarity degree analysis unit 160. In a case where the acquired cause-effect sentence does not include a cause expression or an effect expression, the keyword search unit 140 does not supply the cause-effect sentence to the similarity degree analysis unit 160.

The important cause-effect sentence extraction unit 123 may be configured to extract a cause-effect sentence of which the degree of importance is equal to or greater than a predetermined threshold, and to store the cause-effect sentence in a database (not shown). In this case, the keyword search unit 140 extracts a cause-effect sentence of which the degree of similarity is to be analyzed (calculated) on the basis of the cause-effect sentence stored in the database and the reference information acquired by the acquisition unit 130. Thus, it is possible to reduce a time necessary for the processing of the cause-effect sentence analysis device 10, compared with a case where the important cause-effect sentence extraction unit 123 extracts a cause-effect sentence whenever the keyword search unit 140 performs the processing.

The similarity determination model construction unit 150 constructs a learning model that outputs a value indicating the degree of similarity between a cause expression and a reference expression (hereinafter, referred to as a cause similarity degree) and a value indicating the degree of similarity between an effect expression and the reference expression (hereinafter, referred to as an effect similarity degree), for an input cause-effect sentence to be analyzed, in the patent document information 41 stored in the database 40, using a similarity degree model (for example, word2vec) based on a vector compressed by a dimensional compression technique.

The similarity degree analysis unit 160 acquires a cause-effect sentence supplied from the keyword search unit 140. The similarity degree analysis unit 160 acquires reference expression information acquired by the query acquisition unit 132. The similarity degree analysis unit 160 analyzes (calculates) the similarity degree between a cause expression of the acquired cause-effect sentence and a cause expression of the reference expression (hereinafter, referred to as a cause similarity degree) and the similarity degree between an effect expression of the cause-effect sentence and an effect expression of the reference expression (hereinafter, referred to as an effect similarity degree) by a learning model on the basis of the reference expression information. This learning model refers to a learning model constructed by the similarity determination model construction unit 150.

The desired cause-effect sentence extraction unit 170 extracts a desired cause-effect sentence on the basis of a cause similarity degree and an effect similarity degree calculated by the similarity degree analysis unit 160. The desired cause-effect sentence is, for example, a cause-effect sentence that has a similar cause expression and a non-similar effect expression with respect to a reference expression. Specifically, the desired cause-effect sentence extraction unit 170 extracts a cause-effect sentence in which one of a cause similarity degree and an effect similarity degree is equal to or greater than a first threshold (hereinafter, a threshold TH1) and the other thereof is equal to or smaller than a second threshold (hereinafter, a threshold TH2). Here, in the threshold value TH1 and the threshold value TH2, the threshold value TH1 is a larger value. The desired cause-effect sentence extraction unit 170 extracts, for example, a cause-effect sentence of which a cause similarity degree with respect to a reference expression is equal to or greater than the threshold TH1 and an effect similarity degree is equal to or smaller than the threshold TH2, among the cause-effect sentences of which the degree of similarity is analyzed by the similarity degree analysis unit 160. The desired cause-effect sentence extraction unit 170 extracts, for example, a cause-effect sentence of which an effect similarity degree with respect to the reference expression is equal to or greater than the threshold TH1 and a cause similarity degree is equal to or smaller than the threshold TH2, among the cause-effect sentences of which the degree of similarity is analyzed by the similarity degree analysis unit 160. In addition, the desired cause-effect sentence extraction unit 170 does not extract a cause-effect sentence of which both a cause similarity degree and an effect similarity degree are smaller than the threshold value TH1 and a cause-effect sentence of which both a cause similarity degree and an effect similarity degree are greater than the threshold value TH2. The threshold value TH1 is an example of a first threshold value. The threshold value TH2 is an example of a second threshold value.

The priority assigning unit 180 assigns a priority to a patent document that is an extraction source of a cause-effect sentence on the basis of a cause similarity degree of a cause-effect sentence and an effect similarity degree extracted by the desired cause-effect sentence extraction unit 170.

The priority assigning unit 180 assigns a high priority to a patent document including a cause-effect sentence having a high cause similarity degree and a low effect similarity degree, for example. Here, in a case where there are a plurality of cause-effect sentences that meet a condition, the priority assigning unit 180 assigns a higher priority to a patent document with a lower effect similarity degree among patent documents including a cause-effect sentence having a high cause similarity degree and a low effect similarity degree. Thus, it is possible to assign a high priority to a patent document in which one expression (in this case, the cause expression) is similar to a reference expression and the other expression (in this case, the effect expression) is more dissimilar to the reference expression. The priority assigning unit 180 assigns a high priority to a patent document including a cause-effect sentence having a high effect similarity degree and a low cause similarity degree, for example. Here, in a case where there are a plurality of cause-effect sentences that meet a condition, the priority assigning unit 180 assigns a higher priority to a patent document with a lower cause similarity degree among patent documents including a cause-effect sentence having a high effect similarity degree and a low cause similarity degree. Thus, it is possible to assign a high priority to a patent document in which one expression (in this case, the effect expression) is similar to a reference expression and the other expression (in this case, the cause expression) is more dissimilar to the reference expression. The priority assigning unit 180 assigns a low priority to a patent document including a cause-effect sentence having a low cause similarity degree and a low effect similarity degree, for example. The priority assigning unit 180 supplies information indicating a priority assigned to a cause-effect sentence to the output unit 190.

The output unit 190 acquires information indicating a priority from the priority assigning unit 180. The output unit 190 causes the display unit 20 to display an image of a patent document including a cause-effect sentence determined by the desired cause-effect sentence extraction unit 170 to be a cause-effect sentence having a high cause similarity degree and a low effect similarity degree, on the basis of the acquired information indicating the priority. Further, the output unit 190 causes the display unit 20 to display an image of a patent document including a cause-effect sentence determined by the desired cause-effect sentence extraction unit 170 to be a cause-effect sentence having a high effect similarity degree and a low cause similarity degree, on the basis of the acquired information indicating the priority. More specifically, the output unit 190 causes the display unit 20 to display an image in which patent documents are disposed in the order of patent documents to which higher priorities are assigned.

FIG. 4 is a diagram showing an example of an image displayed on the display unit 20 according to the embodiment. The priority assigning unit 180 assigns priorities of "1" to "5" to cause-effect sentences on the basis of, for example, a cause similarity degree and an effect similarity degree. The output unit 190 disposes and displays patent documents (in the shown example, application numbers of the patent documents) in the order of patent documents to which higher priorities are assigned.

The output unit 190 outputs information relating to a cause-effect sentence extracted by the desired cause-effect sentence extraction unit 170.

In an example of the present embodiment, the output unit 190 causes the display unit 20 to display an image indicating identification information of a patent document including a cause-effect sentence determined by the similarity degree analysis unit 160 to meet a determination condition.

Further, a case where the output unit 190 causes the display unit 20 to display an image disposed in the order of patent documents to which higher priorities are assigned has been described, but the invention is not limited thereto. For example, a configuration in which the output unit 190 causes the display unit 20 to display an image disposed in the order of patent documents to which lower priorities are assigned may be used. Further, a configuration in which the output unit 190 causes the display unit 20 to display an image indicating a patent document to which a priority equal to or greater than a predetermined threshold is assigned among patent documents including a cause-effect sentence determined by the similarity degree analysis unit 160 to meet a determination condition may be used.

Further, in the above description, a case where the output unit 190 displays patent documents disposed in the order of patent documents to which higher priorities are assigned has been described, but the invention is not limited thereto. For example, a configuration in which the output unit 190 displays an image in which a flag is set on a patent document to which a high priority is assigned may be used.

Further, a configuration in which the output unit 190 emphasizes and displays a patent document to which a high priority is assigned may be used.

In the above description, a case where the output unit 190 causes the display unit 20 to display an image indicating an identification number (in this example, an application number) of a patent document including a cause-effect sentence acquired from the desired cause-effect sentence extraction unit 170 has been described, but the invention is not limited thereto. A configuration in which the output unit 190 causes the display unit 20 to display an image indicating a patent document including a cause-effect sentence acquired from the desired cause-effect sentence extraction unit 170 may be used, further, a configuration in which the output unit 190 causes the display unit 20 to display information indicating a storage location in the database 40 of a patent document including a cause-effect sentence acquired from the desired cause-effect sentence extraction unit 170 may be used.

[Operation of Cause-Effect Sentence Analysis Device]

Hereinafter, an operation of the cause-effect sentence analysis device 10 will be described in detail with reference to FIG. 5.

Figure 5:
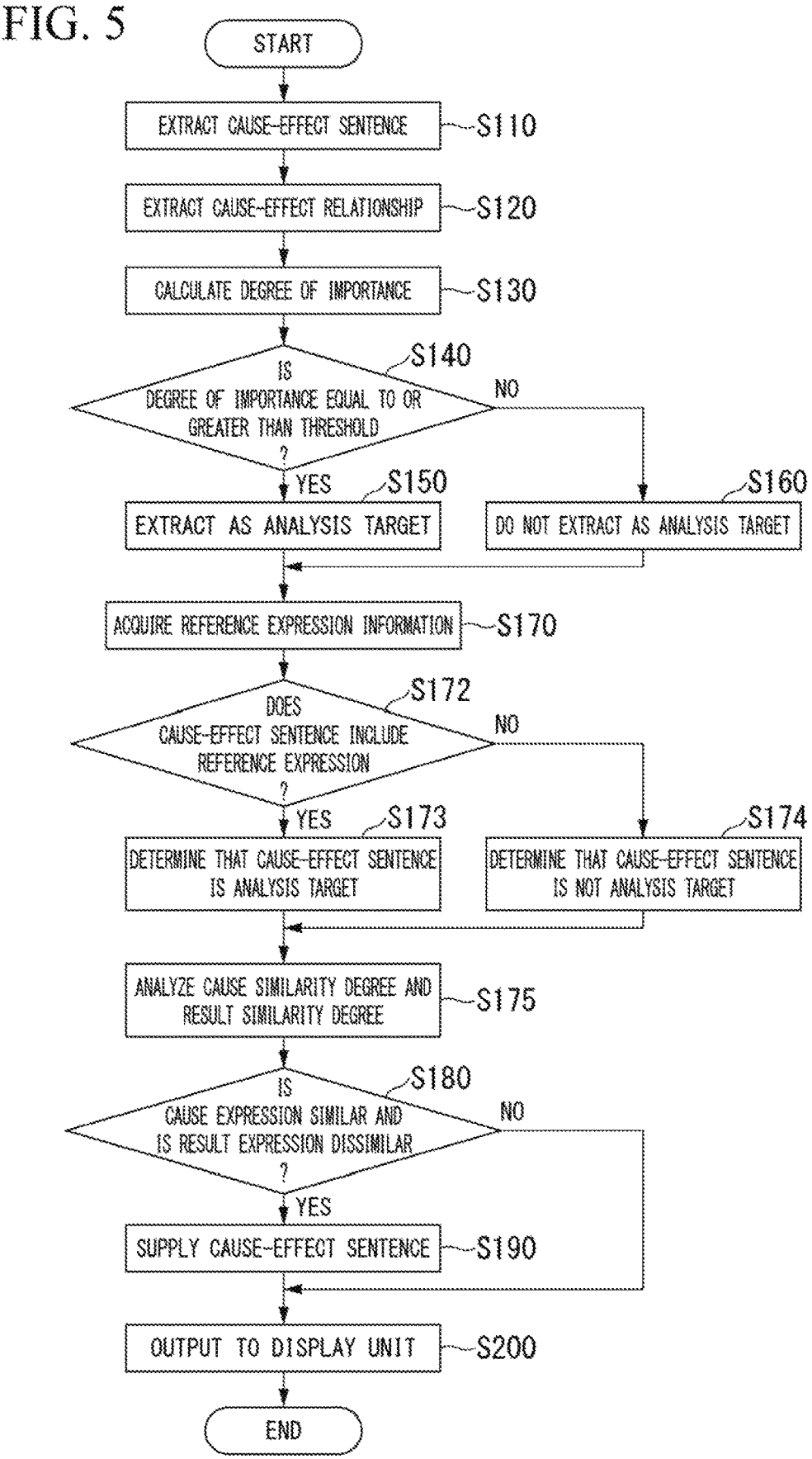
FIG. 5 is a flowchart showing an example of an operation of a cause-effect sentence analysis device according to the embodiment.

FIG. 5 is a flowchart showing an example of an operation of the cause-effect sentence analysis device 10 according to the embodiment.

The cause-effect sentence extraction unit 110 extracts a cause-effect sentence included in a patent document indicated by the patent document information 41 (step S110). Here, the cause-effect sentence extraction unit 110 supplies information indicating the cause effect sentence and identification information of the patent document from which the cause-effect sentence is extracted to the noise removing unit 120. The cause-effect relationship extraction unit 121 included in the noise removing unit 120 extracts a cause-effect sentence that meets a predetermined condition from the cause-effect sentences extracted by the cause-effect sentence extraction unit 110 (step S120).

[Example of Cause-Effect Sentence Extraction by Cause-Effect Relationship Extraction Unit]

Hereinafter, an example of a cause-effect sentence extracted by the cause-effect relationship extraction unit 121 will be described with reference to FIGS. 6 and 7.

FIG. 6 is a diagram showing an example of a cause-effect sentence that meets a predetermined condition according to the embodiment.

FIG. 7 is a diagram showing an example of a cause-effect sentence that does not meet the predetermined condition according to the embodiment.

With the above-described configuration, the cause-effect sentence extraction unit 110 extracts a cause-effect sentence from a patent document (sentences TX1 to TX4 in the figure). Here, there is a case where, even in a case where a cause-effect sentence includes a cause expression including a cause-effect verb and an effect expression including a consequent verb in the order of the cause expression and the effect expression, the cause-effect sentence is not a cause-effect sentence in which the cause expression indicates a problem of an invention and the effect expression indicates an effect of the invention (sentences TX3 to TX4 in the figure). The cause-effect relationship extraction unit 121 extracts a cause-effect sentence to be analyzed on the basis of a cause-effect sentence score (hereinafter, referred to as a score SC). The cause-effect relationship extraction unit 121 calculates a score SC (SC1 to SC4 shown in the figure) for each extracted cause-effect sentence by, for example, machine learning using teacher data such as a support vector machine. In this example, the cause-effect relationship extraction unit 121 extracts a cause-effect sentence (sentences TX1 to TX2 shown in the figure) having a positive score SC value from among the sentences TX1 to TX4 as a cause-effect sentence to be analyzed by the similarity degree analysis unit 160. Further, the cause-effect relationship extraction unit 121 excludes a cause-effect sentence (sentences TX3 to TX4 shown in the figure) having a negative score SC value from the sentence TX1 to TX4 from the cause-effect sentence to be analyzed by the similarity degree analysis unit 160.

Returning to FIG. 5, the importance degree calculation unit 122 calculates the degree of importance of a cause-effect sentence extracted by the cause-effect relationship extraction unit 121 (step S130).

[Example of Importance Degree Calculation by Importance Degree Calculation Unit]

Hereinafter, an example of the degree of importance of a cause-effect sentence calculated by the importance degree calculation unit 122 will be described with reference to FIG. 8.

FIG. 8 is a diagram showing an example of calculation of the degree of importance of a cause-effect sentence according to the embodiment.

As shown in FIG. 8, in this example, a case where a cause-effect sentence extracted by the cause-effect relationship extraction unit 121 is a sentence of "it is possible to prevent attachment of adhesive substances, and to finish maintenance to the minimum" will be described. The importance degree calculation unit 122 refers to information indicating the degree of importance of a patent document from which a cause-effect sentence is extracted, from the importance degree information 51. For example, the importance degree calculation unit 122 searches for the importance degree information 51 using identification information of a patent document acquired from the cause-effect sentence extraction unit 110 as a search key. The importance degree calculation unit 122 refers to the degree of importance of each word associated with the identification information that matches the search key. As shown in FIG. 8, in this example, of the patent document, the degree of importance of "adhesive substances" is "3.0", the degree of importance of "attachment" is "1.0", and the degree of importance of "prevent" is "1.0", the degree of importance of "maintenance" is "5.0", the degree of importance is "minimum" is "3.0", and the degree of importance of "finish" is "0.5". The cause-effect relationship extraction unit 121 calculates the sum of the degrees of importance included in the cause expression (in this example, "5.0") as the degree of importance of the cause expression. Further, the cause-effect relationship extraction unit 121 calculates the sum of the degrees of importance included in the effect expression (in this example, "8.5") as the degree of importance of the effect expression.

Returning to FIG. 5, the important cause-effect sentence extraction unit 123 extracts a cause-effect sentence to be analyzed by the similarity degree analysis unit 160 among the cause-effect sentences extracted by the cause-effect relationship extraction unit 121 on the basis of the degree of importance calculated by the importance degree calculation unit 122 (step S140). Specifically, in a case where the degree of importance of each of the cause expression and the effect expression is equal to or greater than a predetermined threshold (step S140; YES), the important cause-effect sentence extraction unit 123 extract the cause-effect sentence as the cause-effect sentence to be analyzed by the similarity degree analysis unit 160 (step S150). In a case where the degree of importance of each of the cause expression and the effect expression is smaller than the predetermined threshold (step S140; NO), the importance degree calculation unit 122 does not extract the cause-effect sentence as the cause-effect sentence to be analyzed by the similarity degree analysts unit 160 (step S160).

The acquisition unit 130 acquires reference expression information indicating a reference expression on the basis of an operation on the operation unit 30 by the keyword acquisition unit 131 and the query acquisition unit 132 (step S170). The keyword search unit 140 determines whether or not the cause-effect sentence extracted by the important cause-effect sentence extraction unit 123 includes the reference expression information acquired by the acquisition unit 130 (step S172). In a case where the cause-effect sentence includes the reference expression information (step S172; YES), the keyword search unit 140 determines that the cause-effect sentence is the cause-effect sentence to be analyzed by the similarity degree analysis unit 160 (step S173). In a case where the cause-effect sentence does not include the reference expression information (step S172; NO), the keyword search unit 140 determines that the cause-effect sentence is not the cause-effect sentence to be analyzed by the similarity degree analysis unit 160 (step S174).

The similarity degree analysis unit 160 calculates a cause similarity degree and an effect similarity degree, for example, using a learning model constructed by the similarity determination model construction unit 150. The similarity degree analysis unit 160 determines whether or not the cause-effect sentence acquired from the keyword search unit 140 is a cause-effect sentence having a high cause similarity degree and a low effect similarity degree compared with the reference expression (step S150). In a case where the cause-effect sentence acquired from the keyword search unit 140 is the cause-effect sentence having the high cause similarity degree and the low effect similarity degree compared with the reference expression (step S180; YES), the similarity degree analysis unit 160 supplies information indicating the cause-effect sentence to the output unit 190 (step S190). In a case where the cause-effect sentence acquired from the important cause-effect sentence extraction unit 123 is not the cause-effect sentence having the high cause similarity degree and the low effect similarity degree compared with the reference expression (step S180; NO), the similarity degree analysis unit 160 does not supply the information indicating the cause-effect sentence to the output unit 190, and the procedure proceeds to step S200. The output unit 190 outputs the information indicating the cause-effect sentence acquired from the similarity degree analysis unit 160. In this example, the output unit 190 causes the display unit 20 to display an image indicating a patent publication gazette number and an unexamined patent application publication gazette number of a patent document including the cause-effect sentence acquired from the similarity degree analysis unit 160 (step S200).

FIG. 9 is a diagram showing an output example of a cause-effect sentence according to the embodiment.

Specifically, FIG. 9 is a diagram showing an example of a cause-effect sentence output by the output unit 190. As shown in FIG. 9, as the user inputs a cause-effect sentence into the operation unit 30 as a query, the cause-effect sentence analysis device 10 extracts a cause-effect sentence having a similar cause expression and a non-similar effect expression.

[Determination of Patent Document in which Different Configurations of Invention are Disclosed]

Further, the similarity degree analysis unit 160 may determine whether or not a cause-effect sentence includes an effect expression having a high similarity degree compared with the reference expression and a cause expression having a low similarity degree compared with the reference expression.

In this case, the similarity degree analysis unit 160 determines whether or not the cause-effect sentence acquired from the important cause-effect sentence extraction unit 123 is a cause-effect sentence having a high effect similarity degree and a low cause similarity degree. In a case where the cause-effect sentence acquired from the importance degree calculation unit 122 is the cause-effect sentence having the high effect similarity degree and the low cause similarity degree, the similarity degree analysis unit 160 supplies information indicating the cause-effect sentence to the output unit 190. In a case where the cause-effect sentence acquired from the importance degree calculation unit 122 is not the cause-effect sentence with the high effect similarity degree and the low-cause similarity degree, the similarity degree analysis unit 160 does not supply the information indicating the cause-effect sentence to the output unit 190.

Summary of Embodiment

As described above, the cause-effect sentence analysis device 10 according to the present embodiment includes the cause-effect sentence extraction unit 110 that extracts a cause-effect sentence including a cause expression and an effect expression from a text, the acquisition unit 130 that acquires information indicating a reference expression serving as a reference for analyzing the degree of similarity, the similarity degree analysis unit 160 that calculates a cause similarity degree, namely, the degree of similarity between the cause expression included in the cause-effect sentence and the reference expression, and an effect similarity degree, namely, the degree of similarity between the reference expression and the effect expression included in the cause-effect sentence, for the cause-effect sentence extracted by the cause-effect sentence extraction unit 110, and the desired cause-effect sentence extraction unit 170 that extracts a cause-effect sentence in which one of the cause expression and the effect expression included in the cause-effect sentence is similar to the reference expression and the other thereof is not similar to the reference expression. The cause-effect sentence analysis device 10 of the present embodiment may determine a cause-effect sentence having a part that is similar and the other part that is dissimilar, and may specify a patent document including the cause-effect sentence. As an effect, the cause-effect sentence analysis device 10 of the present embodiment may specify a patent document relating to an invention having the same configuration and obtaining a different effect. Further, the cause-effect sentence analysis device 10 may specify a patent document relating to an invention having the same effect and having a different configuration. That is, according to the cause-effect sentence analysis device 10 of the present embodiment, a user of a patent literature can extract a patent document that meets a desired condition.

Further, the cause-effect sentence analysis device 10 according to the present embodiment includes a cause-effect relationship extraction unit (in this example, the noise removing unit 120) that extracts a cause-effect sentence that meets a predetermined condition from cause-effect sentences extracted by the cause-effect sentence extraction unit 110. The cause-effect relationship extraction unit 121 of the noise removing unit 120 extracts the cause-effect sentence that meets the predetermined condition from the cause-effect sentences extracted by the cause-effect sentence extraction unit 110. The cause-effect sentence that meets the predetermined condition is, for example, a cause-effect sentence in which a cause expression indicates a problem of an invention and an effect expression indicates an effect of the invention.

Here, there is a case where, even in a case where the cause-effect sentence extracted by the cause-effect sentence extraction unit 110 is a cause-effect sentence including a cause expression including a cause-effect verb and an effect expression including a consequent verb, the cause expression does not indicate a problem of an invention or the effect expression does not indicate an effect of the invention. In this case, in the cause-effect sentence analysis device 10, the processing load for determining the cause-effect sentence becomes large.

On the other hand, since, in the cause-effect sentence analysis device 10 of the present embodiment, since the cause-effect relationship extraction unit 121 extracts a cause-effect sentence that meets a predetermined condition from cause-effect sentences extracted by the cause-effect sentence extraction unit 110 and a cause-effect sentence that does not meet the predetermined condition is excluded from the determination target, it is possible to reduce the processing load associated with the determination of the cause-effect sentence.

Further, the importance degree calculation unit 122 of the cause-effect sentence analysis device 10 of the present embodiment calculates the degree of importance of the cause-effect sentence extracted by the cause-effect relationship extraction unit 121. In addition, the important cause-effect sentence extraction unit 123 extracts a cause-effect sentence of which the degree of importance is equal to or greater than a predetermined threshold as a cause-effect sentence to be analyzed by the similarity degree analysis unit 160 on the basis of the degree of importance calculated by the importance degree calculation unit 122.

Here, there is a case where, even in a case where a cause-effect sentence extracted by the cause-effect sentence extraction unit 110 is a cause-effect sentence including a cause expression including a cause-effect verb and an effect expression including a consequent verb, the cause-effect sentence is not important in view of technical content indicated by a patent, document including the cause-effect sentence. In this case, in the cause-effect sentence analysis device 10, the processing load for determining the cause-effect sentence becomes large.

On the other hand, in the cause-effect sentence analysis device 10 of the present embodiment, since the important cause-effect sentence extraction unit 123 determines a cause-effect sentence of which the degree of importance is equal to or greater than a predetermined threshold among cause-effect sentences extracted by the cause-effect sentence extraction unit 110 as an analysis target of the similarity degree analysis unit 160, it is possible to reduce the processing load associated withe the determination of the cause-effect sentence.

Further, the cause-effect sentence analysis device 10 of the present embodiment includes the query acquisition unit 132. The query acquisition unit 132 according to the present embodiment acquires, as reference expression information, information indicating a cause-effect sentence input as a query through the operation unit 30 by a user. Further, on the basis of the reference expression information acquired by the query acquisition unit 132, the similarity degree analysis unit 160 determines a cause-effect sentence having a part that is similar to the reference expression and a different part that is not similar to the reference expression. Further, the cause-effect sentence analysis device 10 of the present embodiment includes the keyword acquisition unit 131. The keyword acquisition unit 131 acquires, as reference expression information, a set of a keyword indicating a cause expression and a keyword indicating an effect expression, which are keywords input through the operation unit 30 by the user. Further, on the basis of the reference expression information acquired by the keyword acquisition unit 131, the similarity degree analysis unit 160 determines a cause-effect sentence having a part that is similar to the reference expression and a different pan that is not similar to the reference expression.

Thus, the cause-effect sentence analysis device 10 of the present embodiment inputs a query or a keyword of a reference expression that is a reference for determining a cause-effect sentence, and can specify a patent document in a technical field desired by the user, which is a patent document that relates to an invention having the same configuration and capable of obtaining a different effect. Further, the cause-effect sentence analysis device 10 of the present embodiment inputs a query or a keyword of a reference expression that is a reference for determining a cause-effect sentence, and can specify a patent document in a technical field desired by the user, which is a patent document that relates to an invention capable of obtaining the same effect and having a different configuration.

Further, the cause-effect sentence analysis device 10 of the present embodiment includes the priority assigning unit 180. The priority assigning unit 180 assigns a priority to a cause-effect sentence determined by the similarity degree analysis unit 160. The cause-effect sentence analysis device 10 of the present embodiment displays the effect determined by the similarity degree analysis unit 160 on the display unit 20 on the basis of the priority. Here, the cause-effect sentence analysis device 10 may determine that a plurality of patent documents meet a determination condition of the similarity degree analysis unit 160. In this case, there is a possibility that a user of the patent literatures may have the trouble of referring to a patent document that meets the determination condition.

According to the cause-effect sentence analysis device 10 of the present embodiment, the display unit 20 displays the patent literatures in descending order of priority. Accordingly, the user of the patent literatures can easily refer to a desired patent document.

[Method for Calculating Degree of Importance of Cause-Effect Sentence]

In the above description, a case where the importance degree calculation unit 122 calculates the sum of the degrees of importance of words included in a cause-effect sentence as the degree of importance of the cause-effect sentence has been described, but the method for calculating the degree of importance of the cause-effect sentence is not limited thereto. For example, a configuration in which the importance degree calculation unit 122 calculates a value obtained by dividing the sum of the degrees of importance of the words included in the cause-effect sentence by the number of the words included in the cause-effect sentence as the degree of importance of the cause-effect sentence may be used. Thus, the importance degree calculation unit 122 can calculate a normalized value as the degree of importance of the cause-effect sentence regardless of the number of the words included in the cause-effect sentence.

[Another Configuration of Noise Removal]

In the above description, the case where the important cause-effect sentence extraction unit 123 supplies the cause-effect sentence extracted as having the degree of importance equal to or greater than the predetermined threshold value to the similarity degree analysis unit 160 has been described, but the method for supplying information to the similarity degree analysis unit 160 from the important cause-effect sentence extraction unit 123 is not limited thereto. A configuration in which the important cause-effect sentence extraction unit 123 determines whether or not a cause-effect sentence is a cause-effect sentence to be analyzed by the similarity degree analysis unit 160 and supplies information indicating the determined result to the similarity degree analysis unit 160 may be used. In this case, the similarity degree analysis unit 160 determines a cause-effect sentence indicating that the determination result is an analysis target of the similarity degree analysis unit 160 on the basis of the information indicating the determination result acquired from the important cause-effect sentence extraction unit 123.

[Extraction of Reference Expression]

Further, in the above description, a case where the acquisition unit 130 acquires a reference expression such as a query or a keyword input to the operation unit 30 by a user as reference expression information has been described, but the method for acquiring the reference expression is not limited to thereto. A configuration in which the cause-effect sentence analysis device 10 includes, for example, a query extraction unit that extracts a query on the basis of a cause-effect sentence may be used. For example, the query extraction unit extracts a phrase having a high degree of importance as a query with reference to the importance degree information 51 corresponding to a patent document from which a cause-effect sentence is extracted. In addition, the query extraction unit extracts, for example, a frequently-used phrase of a patent document from which a cause-effect sentence is extracted as a query. Thus, the cause-effect sentence analysis device 10 of the present embodiment can reduce a user's effort for examining a query or a keyword as a reference expression. In this case, the acquisition unit 130 is an example of a query extraction unit.

[Case where Noise Removal is not Performed]

In the above description, a case where the noise removing unit 120 excludes cause-effect sentences other than a determination target from cause-effect sentences extracted by the cause-effect sentence extraction unit 110 has been described, but the noise removing method is not limited to thereto. For example, as in a case where the number of cause-effect sentences extracted by the cause-effect sentence extraction unit 110 is small, there is a case where the noise removing unit 120 does not have to exclude the cause-effect sentences other than the determination target.

Further, a configuration in which a cause-effect sentence extracted by the came-effect sentence extraction unit 110 is processed by the importance degree calculation unit 122 and is not processed by the importance degree calculation unit 122 and the important cause-effect sentence extraction unit 123 may be used. In this case, the similarity degree analysis unit 160 may be configured to perform determination for a cause-effect sentence extracted by the cause-effect relationship extraction unit 121 among the cause-effect sentences extracted by the cause-effect sentence extraction unit 110.

Further, a configuration in which a cause-effect sentence extracted by the cause-effect sentence extraction unit 110 is processed by the cause-effect relationship extraction unit 121 and the important cause-effect sentence extraction unit 123 and is not processed by the cause-effect relationship extraction unit 121 may be used. In this case, the similarity degree analysis unit 160 may be configured to perform determination for a cause-effect sentence determined to be analyzed by the similarity degree analysis unit 160 by the important cause-effect sentence extraction unit 123 among the cause-effect sentences extracted by the cause-effect sentence extraction unit 110.

[Method for Calculating the Degree of Importance]

Further, in the above description, a case where the importance degree calculation unit 122 calculates the sum of degrees of importance of respective words included in a cause-effect sentence as the degree of importance of the cause-effect sentence has been described, but the method for calculating the degree of importance is not limited to thereto. For example, a configuration in which in determining a cause-effect sentence having a similar cause expression and a dissimilar effect expression, the importance degree calculation unit 122 calculates the sum of degrees of importance of words included in the cause expression as the degree of importance of the cause-effect sentence may be used. Further, for example, a configuration in which in determining a cause-effect sentence having a similar effect expression and a dissimilar cause expression, the importance degree calculation unit 122 calculates the sum of degrees of importance of words included in the effect expression as the degree of importance of the cause-effect sentence may be used. Thus, the cause-effect sentence analysis device 10, and the cause-effect sentence analysis device 10 can extract a cause-effect sentence to be analyzed with higher accuracy.

It should be noted that the cause-effect sentence analysis device 10 and the respective units provided in the cause-effect sentence analysis device 10 in each of the above-described embodiments may be realized by dedicated hardware, or may be realized by a memory and a microprocessor.

The cause-effect sentence analysis device 10 and the respective units provided in the cause-effect sentence analysis device 10 may be configured by a memory and a CPU (central processing unit), and in this case, a program for realizing the functions of the cause-effect sentence analysis device 10 and the respective units provided in the cause-effect sentence analysis device 10 may be loaded into the memory for execution to realize the functions.

Further, the program for realizing the functions of the cause-effect sentence analysis device 10 and the respective units provided in the cause-effect sentence analysis device 10 may be recorded on a computer-readable recording medium, and the program recorded on the recording medium may be read into a computer system for execution to perform the processing. Here, the "computer system" includes an OS and hardware such as peripheral devices.

The "computer system" also includes a homepage providing environment (or a display environment) in a case where the WWW system is used.

The "computer-readable recording medium" refers to a portable medium such as a flexible disc, a magneto-optical disc, a ROM or a CD-ROM, and a storage device such as a hard disk built in a computer system. Further, it is also assumed that the "computer-readable recording medium" includes a communication line for transmitting a program through a network such as the Internet or a communication line such as a telephone line, which dynamically holds the program for a short lime, and a volatile memory in a computer system serving as a server or a client in that case, which holds the program for a certain period of time, for example. Further, the above-mentioned program may realize a part of the above-mentioned functions, or may realize the above-mentioned functions in combination with a program already recorded in a computer system.

In the above description, a case where a text to be analyzed by the cause-effect sentence analysis system 1 is a patent document has been described, but the invention is not limited to thereto. The document to be analyzed by the cause-effect sentence analysis system 1 may be any document as long as it includes a cause-effect sentence. The document to be analyzed by the cause-effect sentence analysis system 1 may be, for example, a paper, a report, a description, a specification, or other technical texts.

The embodiments of the invention has been described in detail with reference to the drawings, but the specific configurations are not limited to this embodiment, and may be appropriately modified without departing from the concept of the invention. The configurations described in the above embodiments may be combined.

REFERENCE SIGNS LIST

1 Cause-effect sentence analysis system
10 Cause-effect sentence analysis device
20 Display unit
30 Operation unit
40 Database
41 Patent document information
50 Database
51 Importance degree information
100 Control unit
10 Cause-effect sentence extraction unit
120 Noise removing unit
121 Cause-effect relationship extraction unit
122 Importance degree calculation unit
123 Important cause-effect sentence extraction unit
130 Acquisition unit
131 Keyword acquisition unit
132 Query acquisition unit
140 Keyword search unit
150 Similarity determination model construction unit
160 Similarity degree analysis unit
170 Desired cause-effect sentence extraction unit
180 Priority assigning unit
190 Output unit

What is claimed is:

1. A cause-effect sentence analysis device comprising:
at least one processor configured to:
   obtain a text from a database and extract a plurality of cause-effect sentences from the text, wherein each cause-effect sentence includes a cause expression and an effect expression;
   calculate a plurality of importance degrees corresponding to the plurality of cause-effect sentences, wherein the plurality of importance degrees indicate an importance of the plurality of cause-effect sentences with respect to the text;
   select, from among the plurality of cause-effect sentences, a plurality of target cause-effect sentences, wherein an importance degree corresponding to each target cause-effect sentence from among the plurality of target cause-effect sentences is above an importance threshold;
   acquire information indicating a reference expression serving as a reference for analyzing a degree of similarity;
   calculate, for the each target cause-effect sentence, a cause similarity degree that is the degree of similarity between the cause expression included in the target cause-effect sentence and the reference expression and an effect similarity degree that is the degree of similarity between the effect expression included in the target cause-effect sentence and the reference expression, wherein at least one of the cause similarity degree and the effect similarity degree is calculated using a similarity degree model based on a vector representation; and
   select, from among the plurality of target cause-effect sentences, a target cause-effect sentence in which one of the cause similarity degree and the effect similarity degree is above a similarity threshold, and the other of the cause similarity degree and the effect similarity degree is below the similarity threshold,
wherein the importance degree comprises a cause importance degree corresponding to the cause expression and an effect importance degree corresponding to the effect expression, and
wherein the importance degree is determined to be above the importance threshold based on at least one of the cause importance degree being above a cause importance threshold, and the effect importance degree being above an effect importance threshold.

2. The cause-effect sentence analysis device according to claim 1,
wherein the reference expression includes a cause expression and an effect expression.

3. The cause-effect sentence analysis device according to claim 1,
wherein the at least one processor is further configured to select a target cause-effect sentence in which one of the cause similarity degree and the effect similarity degree is equal to or greater than a first threshold and the other thereof is equal to or smaller than a second threshold which is smaller than the first threshold.

4. The cause-effect sentence analysis device according to claim 1, wherein the at least one processor is further configured to:
extract a target cause-effect sentence that meets a predetermined condition from the plurality of cause-effect sentences extracted by the at least one processor, and
calculate the cause similarity degree and the effect similarity degree for the target cause-effect sentence extracted by at least one processor.

5. The cause-effect sentence analysis device according to claim 1, wherein the at least one processor is further configured to:
extract a query on the basis of the plurality of target cause-effect sentences extracted by the at least one processor, and
acquire the query extracted by the at least one processor as the reference expression.

6. The cause-effect sentence analysis device according to claim 1,
wherein the at least one processor is further configured to acquire information input by a user as information indicating the reference expression.

7. The cause-effect sentence analysis device according to claim 1,
wherein the at least one processor is further configured to acquire information indicating a keyword input to the cause-effect sentence analysis device by the user as information indicating the reference expression.

8. The cause-effect sentence analysis device according to claim 1, wherein the at least one processor is further configured to:
assign a priority on the basis of the cause similarity degree and the effect similarity degree to the target cause-effect sentence of which the cause similarity degree and the effect similarity degree are calculated by the at least one processor.

9. The cause-effect sentence analysis device according to claim 1,
wherein the sentence is a sentence included in a patent document.

10. A cause-effect sentence analysis system comprising:
the cause-effect sentence analysis device according to claim 1;
an input interface for inputting information indicating the reference expression; and
a display that is configured to display the target cause-effect sentence output by the cause-effect sentence analysis device.

11. The cause-effect sentence analysis device according to claim 1, wherein the cause importance degree comprises a sum of a plurality of cause importance degrees included in the cause expression, and
wherein the effect importance degree comprises a sum of a plurality of effect importance degrees included in the effect expression.

12. A non-transitory computer-readable medium configured to store instruction which, when executed by at least one processor, cause the at least one processor to execute:
a cause-effect sentence extraction step of obtaining a text from a database and extracting a plurality of cause-effect sentences from the text, wherein each cause-effect sentence includes a cause expression and an effect expression;
an importance degree calculation step of calculating a plurality of importance degrees corresponding to the plurality of cause-effect sentences, wherein the plurality of importance degrees indicate an importance of the plurality of cause-effect sentences with respect to the text;
a selection step of selecting, from among the plurality of cause-effect sentences, a plurality of target cause-effect sentences, wherein an importance degree corresponding to each target cause-effect sentence from among the plurality of target cause-effect sentences is above an importance threshold;
an acquisition step of acquiring information indicating a reference expression serving as a reference for analyzing a degree of similarity;
a similarity degree analysis step of calculating, for the target each cause-effect sentence, a cause similarity degree that is the degree of similarity between the cause expression included in the target cause-effect sentence and the reference expression and an effect similarity degree that is the degree of similarity between the effect expression included in the target cause-effect sentence and the reference expression, wherein at least one of the cause similarity degree and the effect similarity degree is calculated using a similarity degree model based on a vector representation; and
an output step of selecting, from among the plurality of target cause-effect sentences, a target cause-effect sentence in which one of the cause similarity degree and the effect similarity degree is above a similarity threshold, and the other of the cause similarity degree and the effect similarity degree is below the similarity threshold,
wherein the importance degree comprises a cause importance degree corresponding to the cause expression and an effect importance degree corresponding to the effect expression, and
wherein the importance degree is determined to be above the importance threshold based on at least one of the cause importance degree being above a cause importance threshold, and the effect importance degree being above an effect importance threshold.

13. A cause-effect sentence analysis method performed in a computer, comprising:
obtaining a text from a database and extracting a plurality of cause-effect sentences from the text, wherein each cause-effect sentence includes a cause expression and an effect expression;
calculating a plurality of importance degrees corresponding to the plurality of cause-effect sentences, wherein the plurality of importance degrees indicate an importance of the plurality of cause-effect sentences with respect to the text;
selecting, from among the plurality of cause-effect sentences, a plurality of target cause-effect sentences, wherein an importance degree corresponding to each target cause-effect sentence from among the plurality of target cause-effect sentences is above an importance threshold;

acquiring information indicating a reference expression serving as a reference for analyzing a degree of similarity;

performing a similarity degree analysis for calculating, for the each target cause-effect sentence, a cause similarity degree that is the degree of similarity between the cause expression included in the target cause-effect sentence and the reference expression and an effect similarity degree that is the degree of similarity between the effect expression included in the target cause-effect sentence and the reference expression, wherein at least one of the cause similarity degree and the effect similarity degree is calculated using a similarity degree model based on a vector representation; and selecting and outputting, from among the plurality of target cause-effect sentences, a search result comprising a target cause-effect sentence in which one of the cause similarity degree and the effect similarity degree is above a similarity threshold, and the other of the cause similarity degree and the effect similarity degree is below the similarity threshold, wherein the importance degree comprises a cause importance degree corresponding to the cause expression and an effect importance degree corresponding to the effect expression, and wherein the importance degree is determined to be above the importance threshold based on at least one of the cause importance degree being above a cause importance threshold, and the effect importance degree being above an effect importance threshold.

14. A cause-effect sentence analysis device comprising:
at least one processor configured to:
    obtain a text from a database and extract a plurality of cause-effect sentences from the text, wherein each cause-effect sentence includes a cause expression and an effect expression;
    acquire information indicating a reference expression serving as a reference for analyzing a degree of similarity;
    calculate, for the each cause-effect sentence, a cause similarity degree that is the degree of similarity between the cause expression included in the cause-effect sentence and the reference expression and an effect similarity degree that is the degree of similarity between the effect expression included in the cause-effect sentence and the reference expression, wherein at least one of the cause similarity degree and the effect similarity degree is calculated using a similarity degree model based on a vector representation;
    select, from among the plurality of cause-effect sentences, a cause-effect sentence in which one of the cause similarity degree and the effect similarity degree is above a similarity threshold, and the other of the cause similarity degree and the effect similarity degree is below the similarity threshold;
    assign a priority on the basis of the cause similarity degree and the effect similarity degree to the cause-effect sentence of which the cause similarity degree and the effect similarity degree are calculated by the at least one processor; and
    assign the priority to a cause-effect sentence having an effect similarity degree that is above the similarity threshold and a cause similarity degree that is below the similarity threshold from among the plurality of cause-effect sentences, in an ascending order of the cause similarity degree.

15. A cause-effect sentence analysis device comprising:
at least one processor configured to:
    obtain a text from a database and extract a plurality of cause-effect sentences from the text, wherein each cause-effect sentence includes a cause expression and an effect expression;
    acquire information indicating a reference expression serving as a reference for analyzing a degree of similarity;
    calculate, for the each cause-effect sentence, a cause similarity degree that is the degree of similarity between the cause expression included in the cause-effect sentence and the reference expression and an effect similarity degree that is the degree of similarity between the effect expression included in the cause-effect sentence and the reference expression, wherein at least one of the cause similarity degree and the effect similarity degree is calculated using a similarity degree model based on a vector representation;
    select, from among the plurality of cause-effect sentences, a cause-effect sentence in which one of the cause similarity degree and the effect similarity degree is above a similarity threshold, and the other of the cause similarity degree and the effect similarity degree is below the similarity threshold;
    assign a priority on the basis of the cause similarity degree and the effect similarity degree to the cause-effect sentence of which the cause similarity degree and the effect similarity degree are calculated by the at least one processor; and
    assign the priority to a cause-effect sentence having a cause similarity degree that is above the similarity threshold and an effect similarity degree that is below the similarity threshold from among the plurality of cause-effect sentences, in an ascending order of the effect similarity degree.

* * * * *